(12) United States Patent
Ruan et al.

(10) Patent No.: US 6,451,252 B1
(45) Date of Patent: Sep. 17, 2002

(54) ODOR REMOVAL SYSTEM AND METHOD HAVING OZONE AND NON-THERMAL PLASMA TREATMENT

(75) Inventors: R. Roger Ruan, Arden Mills; Hongbin Ma; Ling Chen, both of St. Paul; Philip R. Goodrich, New Brighton; Shaobo Deng; Ye Wang, both of St. Paul, all of MN (US)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 09/488,690

(22) Filed: Jan. 20, 2000

(51) Int. Cl.[7] ................................................. B01J 19/08
(52) U.S. Cl. ................ 422/22; 422/186.04; 422/186.07
(58) Field of Search .............................. 422/5, 10, 21, 422/22, 186.07, 186.04

(56) References Cited

U.S. PATENT DOCUMENTS

| | | | |
|---|---|---|---|
| 3,970,905 A | 7/1976 | Itoh et al. ................ 317/262 E |
| 4,244,712 A | 1/1981 | Tongret ........................ 55/124 |
| 4,391,773 A * | 7/1983 | Flanagan ...................... 422/22 |
| 4,780,277 A * | 10/1988 | Tanaka et al. ................... 422/4 |
| 4,863,701 A | 9/1989 | McMurray ............. 422/186.08 |
| 5,370,846 A * | 12/1994 | Yokomi et al. ......... 422/186.07 |
| 5,427,747 A | 6/1995 | Kong et al. .................. 422/186 |
| 5,458,748 A | 10/1995 | Breault et al. .............. 204/177 |
| 5,549,874 A * | 8/1996 | Kamiya et al. ......... 422/186.07 |
| 5,603,893 A * | 2/1997 | Gunderson et al. ........... 422/22 |
| 5,637,198 A * | 6/1997 | Breault ........................ 204/165 |
| 5,670,122 A | 9/1997 | Zamansky et al. .......... 423/210 |
| 5,681,533 A * | 10/1997 | Hiromi ........................ 422/121 |
| 5,695,619 A | 12/1997 | Williamson et al. ........ 204/165 |
| 5,711,147 A | 1/1998 | Vogtlin et al. ................ 60/274 |
| 5,746,984 A | 5/1998 | Hoard ......................... 422/169 |
| 5,750,823 A | 5/1998 | Wofford et al. ............. 588/210 |
| 5,759,497 A * | 6/1998 | Kuzumoto et al. ..... 422/186.07 |
| 5,827,407 A | 10/1998 | Wang et al. .................. 204/164 |
| 5,843,288 A | 12/1998 | Yamamoto ................... 204/164 |
| 5,843,383 A | 12/1998 | Williamson et al. ... 422/186.04 |
| 5,855,855 A | 1/1999 | Williamson et al. ... 422/186.04 |
| 5,871,703 A | 2/1999 | Alix et al. ................... 423/210 |
| 5,891,409 A | 4/1999 | Hsiao et al. ............. 423/239.1 |
| 5,893,267 A | 4/1999 | Vogtkin et al. ............... 60/274 |
| 5,895,558 A | 4/1999 | Spence ........................ 204/164 |
| 5,904,905 A | 5/1999 | Dolezal et al. ......... 422/186.04 |
| 6,146,599 A | 11/2000 | Ruan et al. ............. 422/186.04 |

FOREIGN PATENT DOCUMENTS

| | | | |
|---|---|---|---|
| DE | 19717160 A1 | | 10/1998 |
| EP | 1271554 A1 | | 11/1986 |
| EP | 1495286 | * | 7/1989 |
| EP | 2316017 | | 2/1998 |
| JP | 59-69404 | * | 4/1984 |
| JP | 2-211218 | | 8/1990 |
| JP | 2-211219 | | 8/1990 |
| JP | 4-122417 | | 4/1992 |
| JP | 4-247218 | | 9/1992 |
| JP | 5-15736 | | 1/1993 |
| JP | 10-118448 | | 5/1998 |
| WO | WO 980342 | | 1/1998 |

* cited by examiner

*Primary Examiner*—Robert J. Warden, Sr.
*Assistant Examiner*—Sean E. Conley
(74) *Attorney, Agent, or Firm*—Westman, Champlin & Kelly

(57) ABSTRACT

An odor removal system includes an odorous gas inlet, a treated gas outlet and a gas treatment flow path from the odorous gas inlet to the treated gas outlet. A mixer is coupled in series with the gas treatment flow path and has an ozone inlet coupled to an ozone outlet of an ozone generator. A non-thermal plasma reactor is also coupled in series with the gas treatment flow path.

24 Claims, 3 Drawing Sheets

ODOR REMOVAL SYSTEM AND METHOD HAVING OZONE AND NON-THERMAL PLASMA TREATMENT

BACKGROUND OF THE INVENTION

The present invention relates to systems for removal of odors emitted from animal and food production environments and, more particularly, to ozone and non-thermal plasma reactors for decomposing odorous compounds.

Industries have devoted considerable effort to develop a variety of technologies to reduce odorous emissions from animal and food production facilities. However, these technologies are typically ineffective or too expensive to implement. For example, ozones have been used to remove larger, more unstable compounds from odorous gas emissions. While ozone generators are fairly energy efficient, these types of generators are not effective in removing smaller, more stable odorous compounds such as ammonia and hydrogen sulfide. Alternatively, plasma has been proposed as a means for removing odorous compounds. Plasma is regarded as the fourth state of matter (ionized state of matter). Unlike thermal plasmas, non-thermal plasmas (NTPs) are in gaseous media at near-ambient temperature and pressure out have electron mean energies considerably higher than other gaseous species in the ambient environment. NTP species include electrically neutral gas moleculest charges particles in the form of positive ions, negative ions, free radicals and electrons, and quanta of electromagnetic radiation (photons). These NTP species are highly reactive and can convert odorous compounds to non-odorous compounds or less-odorous compounds through various chemical reaction mechanisms. In contrast to thermal processes (such as thermal plasma), an NTP process directs electrical energy to induce favorable gas chemical reactions, rather than using the energy to heat the gas. Therefore, NTP is much more energy- efficient than thermal plasma.

NTPs can be generated by electric discharge in the gas for injection of electrons into the gas by an electron beam. Electron beams must be accelerated under a high vacuum and then transferred through special windows to the reaction site. The reaction site must be sized with respect to the penetration depth of the electrons It is much more difficult to scale-up the size of an electron beam reactor than electric discharge reactors. Therefore, electron beam reactors are less favored than electric discharge reactors.

Among the various types of electric discharge reactors, pulse corona and dielectric barrier (silent) discharge reactors are very popular for their effectiveness and efficiency. However, pulse corona reactors have the major disadvantage of requiring special pulsed power supplies to initiate the pulse corona. Consequently, dielectric barrier discharge has become a fast growing technology for pollution control.

Cylindrical and planar reactors are two common dielectrical barrier discharge reactor configurations. Both of these configurations are characterized by the presence of one or more insulating layers in a current path between two metal electrodes, in addition to the discharge space. Other dielectric barrier discharge reactors include packed-bed discharge reactors, and surface discharge reactors.

There are several major difficulties in the practical use of dielectric barrier discharge reactors for odorous gas removal. These difficulties include an expensive power supply, low energy efficiency and flow rate, and the blocking of discharge volume by dusts in the feed gas and/or solid mineral compounds produced during the plasma reactions. More effective and economical barrier discharge reactors are desired.

SUMMARY OF THE INVENTION

On aspect of the present invention relates to an odor removal system, which includes an odorous gas inlet, a treated gas outlet and a gas treatment flow path from the odorous gas inlet to the treated gas outlet. A mixer is coupled in series with the gas treatment flow path and has an ozone inlet coupled to an ozone outlet of an ozone generator. A non-thermal plasma reactor is also coupled in series with the gas treatment flow path.

Another aspect of the present invention relates to a non-thermal plasma discharge reactor, which has an inlet and an outlet. A reaction volume is coupled between the inlet and the outlet. A generally planar ground electrode is positioned along one side of the reaction volume and has a plurality of surface non-uniformities adapted to generate a non-uniform plasma within the reaction volume. A generally planar high-voltage electrode is positioned along an opposite side of the reaction volume with respect to the ground electrode and is separated from the reaction volume by a dielectric barrier.

Another aspect of the present invention relates to a non-thermal plasma discharge reactor having an inlet and an outlet. The reaction volume is coupled between the inlet and the outlet. A generally planar ground electrode is positioned along one side of the reaction volume and extends beyond the reaction volume to form a cooling fin external to the reaction volume. A generally planar high-voltage electrode is positioned along an opposite side of the reaction volume with respect to the ground electrode and is separated from the reaction volume by a dielectric barrier.

Yet another aspect of the present invention relates to a method of removing odorous compounds from an odorous gas. The method includes generating an ozone, mixing the odorous gas with the ozone to remove a first portion of the odorous compounds from the odorous gas, and passing the odorous gas through a non-thermal, non-uniform plasma to remove a second portion of the odorous compounds from the odorous gas.

DETAILED DESCRIPTION OF THE ILLUSTRATIVE EMBODIMENTS

Figure 1:
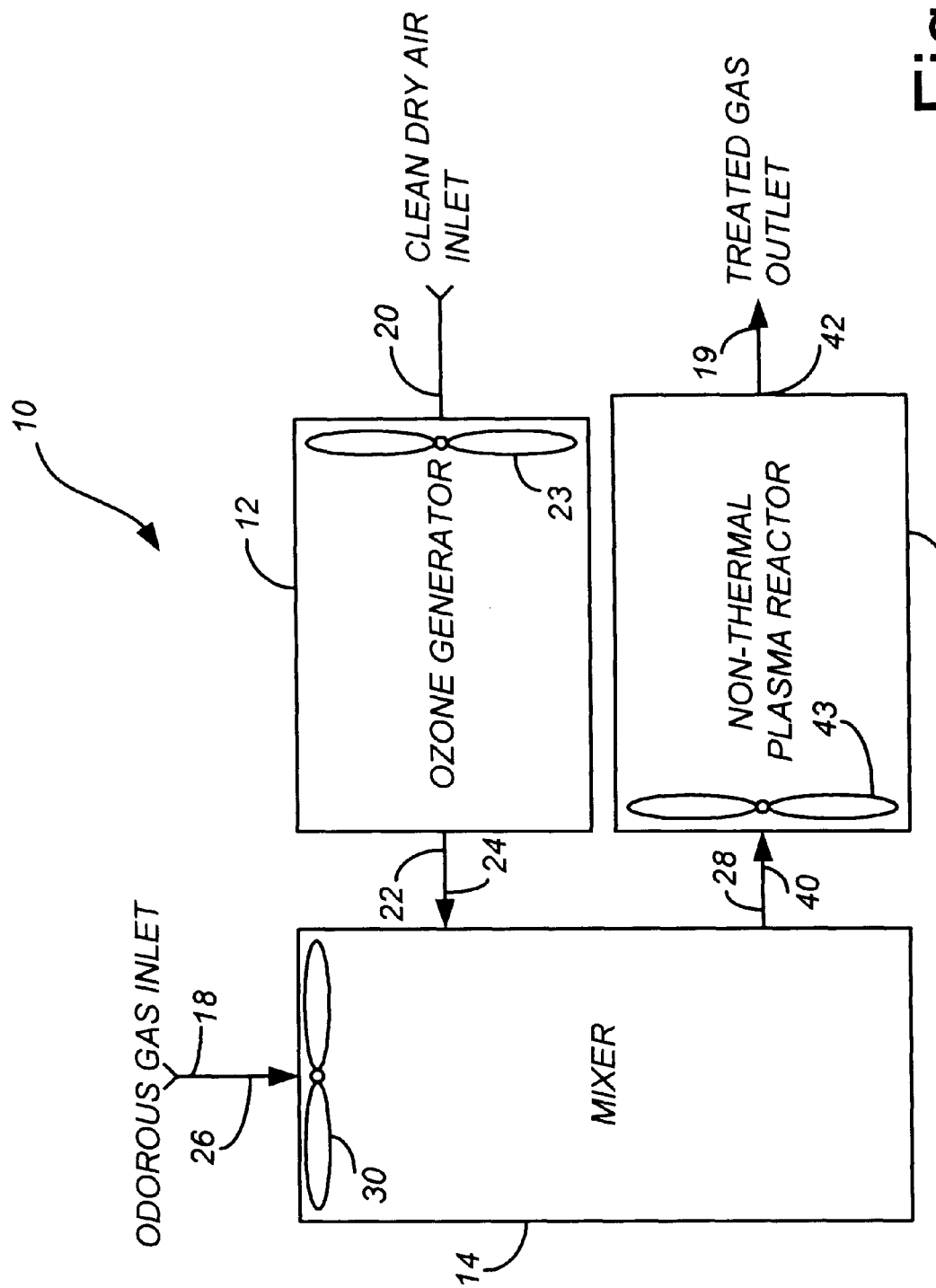
FIG. 1 is a block diagram of an odor removal system according to one embodiment of the present invention.

FIG. 1 is a block diagram of an odor removal system, according to one embodiment of the present invention, which is compact and cost-effective for removing odors emitted from animal and food production environments. Odor removal system 10 includes ozone generator 12, mixer 14 and non-thermal plasma reactor 16. Mixer 14 and reactor 16 are coupled in series with one another within an odorous gas treatment path, which flows from odorous gas inlet 18 to treated gas outlet 19. Mixer 14 and reactor 16 provide a two-step reaction procedure for effectively removing, or decomposing, odorous compounds from the odorous gas received from inlet 18. The treated gas is provided to outlet 19.

Ozone generator 12 has an air inlet 20 for receiving clean, dry air. Ozone generator 12 receives oxygen from air inlet 20 and converts the oxygen to ozone, which is supplied to mixer 14 through ozone outlet 22. A fan 23 can be used to force the clean, dry air from inlet 20 to outlet 22. Mixer 14 has an ozone inlet 24, which is coupled to ozone outlet 22 of ozone generator 12. Mixer 14 further includes an inlet 26, which is coupled to odorous gas inlet 18 for receiving the gas to be treated. In one embodiment, mixer 14 includes a long tube, which facilitates mixing of the odorous gas received from inlet 26 and the ozone received from inlet 24. The ozone supplied through inlet 24 induces favorable chemical reactions in the odorous gas, which decomposes a portion of the odorous compounds from the gas. These compounds are typically larger and relatively unstable compounds such as volatile organic compounds ("VOCs"). The pre-treated gas is then supplied to outlet 28 of mixer 14. A fan 30 can be used to force the odorous gas received from inlet 26 toward outlet 28.

The pre-treated odorous gas is then passed from outlet 28 to inlet 40 of non-thermal plasma reactor 16 for further treatment. Reactor 16 produces various plasma species, which induce further chemical reactions in the pre-treated gas. In one embodiment, reactor 16 is adapted to produce very high-energy, non-uniform "streamer" plasma species, which are effective in decomposing smaller and more stable odorous compounds such as ammonia and hydrogen sulfide. Typical uniform non-thermal plasma species may not produce enough energy to decompose these smaller, more stable compounds. Once the gas has been treated within reactor 16, the treated gas is supplied to treated gas outlet 19 for release into the surrounding environment. A fan 43 can be used, if desired, to force the gas through reactor 16.

Figure 2:
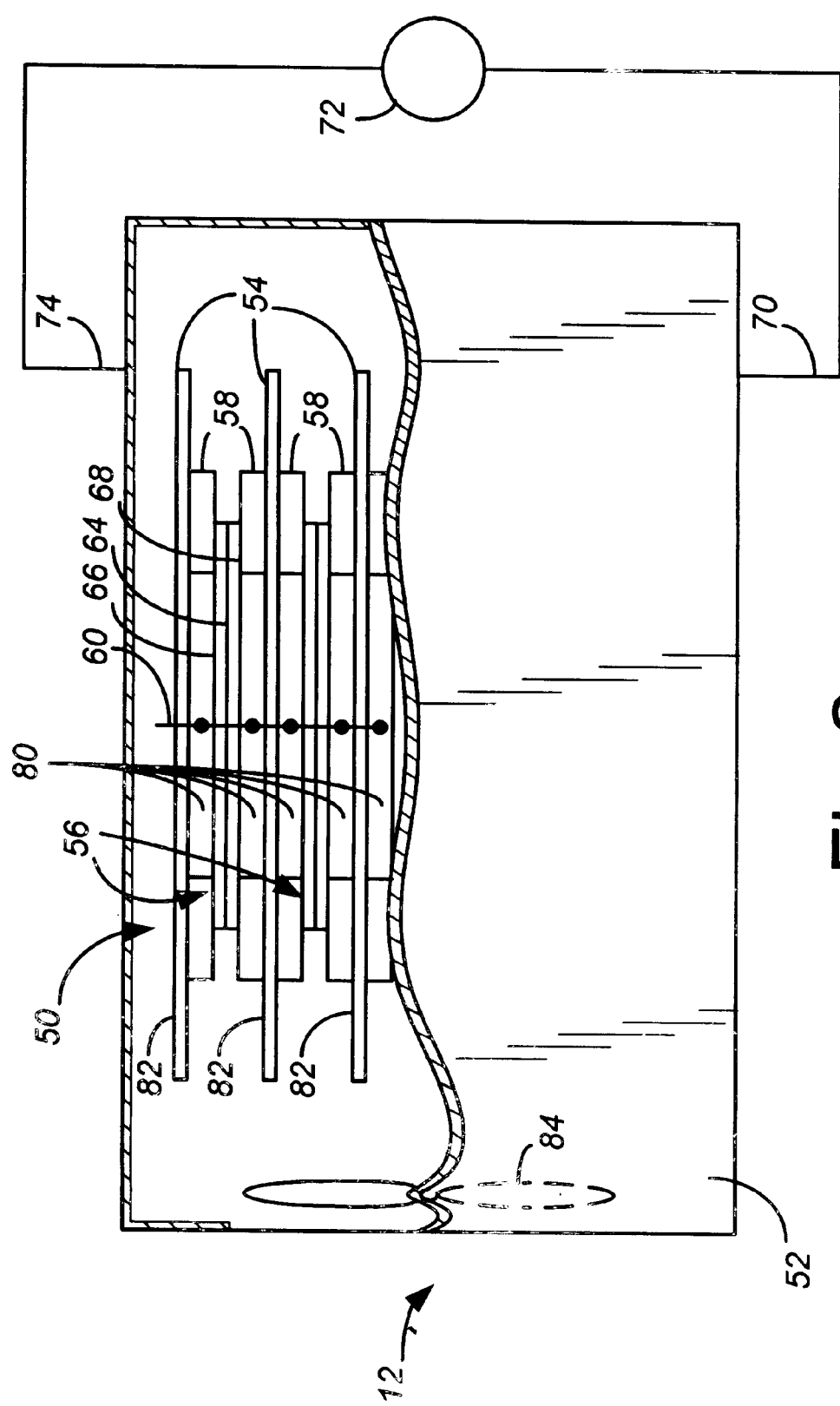
FIG. 2 is a side view of an ozone generator within the system shown in FIG. 1, according to one embodiment of the present invention.

FIG. 2 is a end view of ozone generator 12, as seen from air inlet 20 according to one embodiment of the present invention. Ozone generator 12 includes a non-thermal plasma reactor 50, which is enclosed by a housing 52. A portion of housing 52 is removed for clarity. Reactor 50 is a "silent" electrical discharge-type reactor, which includes a plurality of ground electrode panels 54 and a plurality of interleaved, high-voltage electrode panels 56. The ground and high-voltage electrode panels 54 and 56 are arranged parallel to one another and are separated by spacers 58 to form a plurality of air passages 60 between adjacent pairs of the panels. Air passages 60 extend in parallel with one another from clean air inlet 20 to ozone outlet 22 (shown in FIG. 1). In an alternative embodiment, air passages 60 are coupled in series with one another to create a serpentine-shaped reaction chamber.

In one embodiment, ground electrode panels 54 are each formed of a thin, conductive metal plate. Alternatively, ground electrode panels 54 can include wire meshes, for example. Other conductive structures can also be used. Each high-voltage electrode panel 56 is formed of a thin, conductive plate 64, which is embedded between two opposing layers of dielectric material 66 and 68. For example, each conductive plate 64 can include a thin sheet of copper foil. Other conductor structures can also be used. The layers of dielectric material 66 and 68 can include Teflon, glass, or epoxy resin, for example. In one embodiment, each conductive plate 64 is embedded within an epoxy resin. The layers of dielectric material 66 and 68 form dielectric barriers between the conductors in the high-voltage electrode panels and the adjacent air passages.

Ground electrode panels 54 are electrically coupled to terminal 70 of power supply 72. The conductors in high-voltage electrode panels 56 are electrically coupled to terminal 74 of power supply 72. Adjacent pairs of the electrode panels 54 and 56 therefore have opposite polarity. Power supply 72 can include a direct-current (DC) or an alternating-current (AC) power supply that is capable of producing a voltage across respective pairs of the electrode panels. In one embodiment, the voltage potential generated between electrode panels 54 and 56 is in the range of 1–25 kV, for example. Other voltage ranges can also be used.

The separation between adjacent electrode panels 54 and 56 defines individual reaction volumes 80, which are bounded by spacers 58. In one embodiment, the separation between adjacent electrode panels is 0–20 mm. With each electrode panel 52 and 56 having opposite polarity, excitation of electrode panels 54 and 56 generates an electrical discharge path from each electrode panel to its next adjacent electrode panel, across the reaction volumes 80. The electrical discharge generates non-thermal plasma species, which include electrically neutral gas molecules, charged particles in the form of positive ions, negative ions, free radicals and electrons and quanta of electromagnetic radiation (photons). These non-thermal plasma species are highly reactive and convert the oxygen in the clean, dry air passing though the reaction volumes 80 into high concentrations of ozone, which is supplied to ozone outlet 22 (shown in FIG. 1).

The efficiency of the reactions in reactor 50 are greatly increased, according to one embodiment of the present invention, by extending ground electrode panels 54 beyond reaction volumes 80 to form cooling fins 82 that are external to the reaction volumes 80. Cooling fins 82 greatly improve the cooling of ground electrode panels 54. A fan 84 can be used to provide additional air flow across cooling fins 82 to further increase cooling, if desired.

Figure 3:
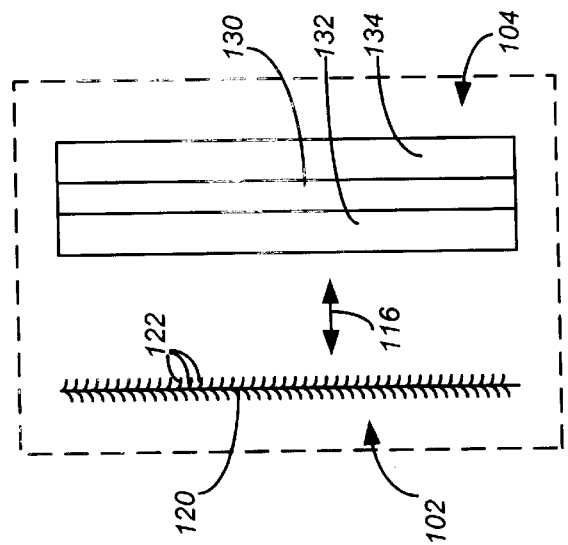
FIG. 3 is a side view of a non-uniform, non-thermal plasma reactor within the system shown in FIG. 1, according to one embodiment of the present invention.

FIG. 3 is a end view of non-thermal plasma reactor 16, as seen from inlet 40 (shown in FIG. 1) according to one embodiment of the present invention. Reactor 16 is enclosed by a housing 100. A portion of housing 100 is removed for clarity. Reactor 16 is a "silent" electrical discharge-type reactor, which includes a plurality of ground electrode panels 102 and a plurality of interleaved, high-voltage electrode panels 104. The ground and high-voltage electrode panels 102 and 104 are arranged parallel to one another and are separated by spacers (not shown) that can be similar to the spacers shown in FIG. 2. The separation between adjacent electrode panels 102 and 104 forms a plurality of air passages 106, which extend in parallel with one another from inlet 40 to outlet 42 (shown in FIG. 1). In an alternative embodiment, air passages 106 are coupled in series with one another to create a serpentine-shaped reaction chamber.

Ground electrode panels 102 are electrically coupled to terminal 110 of power supply 112, while high-voltage electrode panels 104 are electrically coupled to terminal 114 of power supply 112. Adjacent pairs of the electrode panels 102 and 104 therefore have opposite polarity. Power supply 112 can be the same power supply as power supply 72 shown in FIG. 2 or can be a separate power supply, depending upon the particular application.

Figure 4:
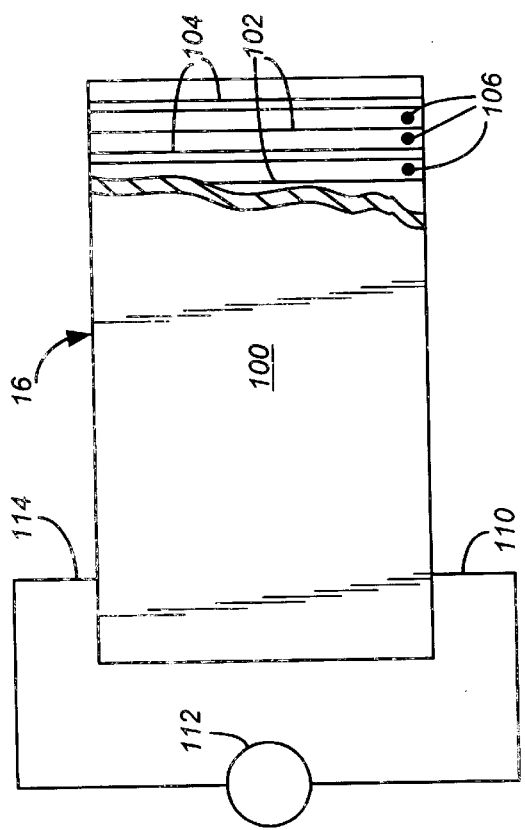
FIG. 4 is a side view of a ground electrode panel within the reactor shown in FIG. 3, according to one embodiment of the present invention.

FIG. 4 is a side view of one of the ground electrode panels 102, according to one embodiment of the present invention. Electrode panel 102 includes a plurality of laterally spaced conductive wires 120, which are electrically coupled to one another. In one embodiment, conductive wires 120 are arranged in a plane and substantially parallel to one another. The wire structure of ground electrode panel 102 provides easy air passages between the wires so that the flow rate through reactor 16 is increased.

Figure 5:
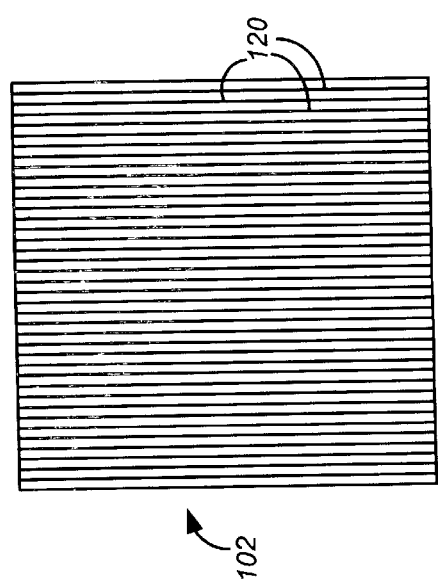
FIG. 5 is a cross-sectional view of a pair of ground and high-voltage electrode panels within the reactor shown in FIG. 3.

FIG. 5 is a cross-sectional view of a pair of ground and high-voltage electrode panels 102 and 104 within reactor 16. Electrodes 102 and 104 are separated by a gap 116, which defines a reaction volume between the electrodes. Each wire 120 includes a plurality of spikes or thorns 122 extending from a surface of the wire. These spikes are adapted to produce very high-energy, non-uniform "streaming" plasma species around the tips of the spikes during electrical discharge across gap 116. These high-energy plasma species are effective in decomposing the smaller, more stable odorous compounds, such as ammonia and hydrogen sulfide. Other non-uniform electrode surface features can also be used in alternative embodiments to generate non-uniform, non-thermal plasma species within the reaction volume. In addition, the wires can be replaced with other conductor structures, such as a wire mesh or a sheet of conductive material that are adapted to generate non-uniform "streaming" plasma species.

High-voltage electrode panel 104 includes a conductive sheet or mesh 130, which is positioned between or embedded within dielectric material 132 and 134. In one embodiment, conductive sheet 130 includes a sheet of copper foil, for example. Other conductive sheets or conductor arrangements can also be used. Dielectric material 132 and 134 can include Teflon, glass or epoxy resin, for example. Other electrical insulators can also be used. However, epoxy resin has been found to provide a very low cost and effective dielectric barrier.

As the gas passes through the reaction volumes of reactor 16, the non-uniform plasma species generated within the reaction volumes decomposes most of the remaining odorous compounds from the gas. The final, treated gas is then supplied to outlet 42 (shown in FIG. 1) of reactor 16 for release into the surrounding environment.

The odor removal system of the present invention provides a compact, cost-effective system for removal of odors emitted from animal and food production environments. The system can be easily installed in facilities used for animal production, dairy, food processing, biological processing, chemical processing, municipal waste treatment facilities and restaurants, for example. The system employs a two-step reaction procedure to effectively remove odorous compounds in gases.

Although the present invention has been described with reference to preferred embodiments, workers skilled in the art will recognize that changes may be made in form and detail without departing from the spirit and scope of the invention. For example, the relative positions of mixer 14 and reactor 16 within the odorous gas treatment path as shown in FIG. 1 can be reversed. Also, the particular electrode structures and arrangements can be modified as desired. The electrode panels can be planar or non-planar. In one embodiment, the electrode panels have a cylindrical shape.

What is claimed is:

1. An odor removal system comprising:
    an odorous gas inlet and a treated gas outlet;
    a gas treatment flow path from the odorous gas inlet to the treated gas outlet;
    an ozone generator having an ozone outlet;
    a mixer coupled in series with the gas treatment flow path and having an ozone inlet coupled to the ozone outlet; and
    a first non-thermal plasma reactor coupled in series with the gas treatment flow path and comprising first and second oppositely polarized electrodes which are separated from one another by a first gap and a first dielectric barrier, wherein the gas treatment flow path flows through the first gap.

2. The odor removal system of claim 1 wherein the ozone generator comprises a second non-thermal plasma reactor, which comprises:
    a ground electrode panel;
    a high-voltage electrode panel, which is parallel to the ground electrode panel and is separated from the ground electrode panel by a second gap; and
    an electrical discharge path, which extends between the ground electrode panel and the high-voltage electrode panel, across the second gap, wherein the gas treatment flow path extends through the electrical discharge path.

3. The odor removal system of claim 2 wherein the high-voltage electrode panel comprises a conductor and a second dielectric barrier positioned between the conductor and the second gap.

4. The odor removal system of claim 3 wherein the second dielectric barrier comprises an epoxy resin, and the conductor is embedded in the epoxy resin.

5. The odor removal system of claim 3 wherein the conductor comprises a planar conductive sheet.

6. The odor removal system of claim 2 wherein:
    the second gap forms a reaction volume between the ground electrode panel and the high-voltage electrode panel; and
    the ground electrode panel extends beyond the reaction volume and forms a cooling fin external to the reaction volume.

7. The odor removal system of claim 6 and further comprising a cooling fan oriented to direct air toward the cooling fin.

8. The odor removal system of claim 2 wherein the ground electrode panel comprises a planar conductive sheet.

9. The odor removal system of claim 2 wherein the second non-thermal plasma reactor further comprises:
    a plurality of ground electrode panels;
    a plurality of high-voltage electrode panels, which are parallel to and interleaved with the plurality of ground electrode panels such that adjacent ones of the ground and high-voltage electrode panels have opposite polarity; and
    a plurality parallel reaction volumes within the gas treatment flow path, wherein each of the reaction volumes is positioned between a respective pair of the ground and high-voltage electrode panels and is within the gas treatment flow path.

10. The odor removal system of claim 1 wherein:
    the first electrode comprises a ground electrode panel;
    the second electrode comprises a high-voltage electrode panel, which is parallel to the ground electrode panel and is separated from the ground electrode panel by the first gap; and
    an electrical discharge path, which extends between the ground electrode panel and the high-voltage electrode panel, across the first gap, wherein the gas treatment flow path extends through the electrical discharge path.

11. The odor removal system of claim 10 wherein the ground electrode panel comprises a plurality of laterally spaced conductive wires, which are electrically coupled to one another.

12. The odor removal system of claim 11 wherein each of the conductive wires comprises a surface and a plurality of conductive spikes extending from the surface.

13. The odor removal system of claim 10 wherein the ground electrode panel has surface features that are adapted to produce non-uniform plasma within the gap when energized to a sufficient voltage potential relative to the high-voltage electrode panel.

14. The odor removal system of claim 10 wherein the ground electrode panel comprises an electrode surface having a plurality of non-uniformities.

15. The odor removal system of claim 10 wherein high-voltage electrode panel comprises a planar conductive sheet, and the first dielectric barrier is positioned between the conductive sheet and the gap.

16. The odor removal system of claim 1 wherein the first non-thermal plasma reactor comprises:
a plurality of ground electrode panels;
a plurality of high-voltage electrode panels, which are parallel to and interleaved with the plurality of ground electrode panels such that adjacent ones of the ground and high-voltage electrode panels have opposite polarity; and
a plurality parallel reaction volumes within the gas treatment flow path, wherein each of the reaction volumes is positioned between a respective pair of the ground and high-voltage electrode panels.

17. A non-thermal plasma discharge reactor comprising:
an inlet and an outlet;
a reaction volume coupled between the inlet and the outlet;
a ground electrode, which is positioned along one side of the reaction volume and comprises a plurality of laterally-spaced wires having surface non-uniformities that are adapted to generate a non-uniform plasma within the reaction volume; and
a generally planar high-voltage electrode, which is positioned along an opposite side of the reaction volume with respect to the ground electrode and is separated from the reaction volume by a dielectric barrier.

18. The non-thermal plasma discharge reactor of claim 17 wherein the plurality of laterally spaced wires are electrically coupled to one another, and wherein each of the wires comprises a plurality of spikes extending from a surface of the wire.

19. The non-thermal plasma discharge reactor of claims 17 wherein the high-voltage electrode comprises a conductive sheet, which is embedded in an epoxy resin, and wherein the epoxy resin forms the dielectric barrier.

20. A non-thermal plasma discharge reactor comprising:
an inlet and an outlet;
a reaction volume coupled between the inlet and the outlet;
a generally planar ground electrode, which is positioned along one side of the reaction volume and extends beyond the reaction volume to form a cooling fin external to the reaction volume; and
a generally planar high-voltage electrode, which is positioned along an opposite side of the reaction volume with respect to the ground electrode and is separated from the reaction volume by a dielectric barrier.

21. A method of removing odorous compounds from an odorous gas, the method comprising:
generating ozone;
mixing the odorous gas with the ozone to remove a first portion of the odorous compounds from the odorous gas; and
passing the odorous gas through a non-thermal, non-uniform plasma after the step of mixing to remove a second portion of the odorous compounds from the odorous gas wherein the plasma is generated within a gap between a ground electrode and a high-voltage electrode and wherein at least one of the electrodes is separated from the gap by a dielectric barrier.

22. The method of claim 21, wherein generating an ozone comprises:
generating a non-thermal plasma and passing clean, dry air through the non-thermal plasma.

23. The method of claim 21, wherein passing the odorous gas through a non-thermal, non-uniform plasma comprises:
applying a voltage potential between the ground electrode and the high-voltage electrode, which are separated by a reaction volume, wherein the ground electrode extends beyond the reaction volume to form a cooling fin and the high-voltage electrode is separated from the reaction volume by the dielectric barrier.

24. The method of claim 21 wherein passing the odorous gas through a non-thermal, non-uniform plasma comprises:
applying a voltage potential between the ground electrode and the high-voltage electrode, which are separated by a reaction volume, to thereby generate the non-thermal plasma, wherein the ground electrode has a plurality of surface non-uniformities that cause the non-thermal plasma to be non-uniform within the reaction volume, and wherein the high-voltage electrode is separated from the reaction volume by the dielectric barrier.

* * * * *

UNITED STATES PATENT AND TRADEMARK OFFICE
CERTIFICATE OF CORRECTION

PATENT NO. : 6,451,252 B1
DATED : September 17, 2002
INVENTOR(S) : R. Roger Ruan et al.

It is certified that error appears in the above-identified patent and that said Letters Patent is hereby corrected as shown below:

Title page,
Item [75], Inventors, address of "R. Roger, Ruan," change "Arden Mills" to
-- Arden Hills --.

Column 7,
Line 47, change "claims" to -- claim --.

Signed and Sealed this

Twenty-ninth Day of April, 2003

JAMES E. ROGAN
*Director of the United States Patent and Trademark Office*